(12) United States Patent
Cohen

(10) Patent No.: US 7,785,339 B2
(45) Date of Patent: Aug. 31, 2010

(54) TOOL FOR CORING PORTIONS OF ONE OR MORE HAIR FOLLICLES

(75) Inventor: Norman S. Cohen, Jacksonville, FL (US)

(73) Assignee: Innovia, LLC, Miami, FL (US)

( * ) Notice: Subject to any disclaimer, the term of this patent is extended or adjusted under 35 U.S.C. 154(b) by 671 days.

(21) Appl. No.: 11/200,404

(22) Filed: Aug. 9, 2005

(65) Prior Publication Data
US 2007/0038236 A1 Feb. 15, 2007

(51) Int. Cl.
*A61B 17/34* (2006.01)
(52) U.S. Cl. .................. 606/187; 606/131; 606/133; 606/179
(58) Field of Classification Search ............... 606/187, 606/133, 167, 131, 132; 600/407; 33/628
See application file for complete search history.

(56) References Cited

U.S. PATENT DOCUMENTS

| | | | | |
|---|---|---|---|---|
| 376,511 | A * | 1/1888 | Carter | 131/255 |
| 2,377,462 | A * | 6/1945 | Tea et al. | 408/111 |
| 3,561,449 | A | 2/1971 | Bellantoni | |
| 4,122,855 | A | 10/1978 | Tezel | |
| 4,210,145 | A | 7/1980 | Nestor et al. | |
| 4,476,864 | A | 10/1984 | Tezel | |
| 4,807,624 | A | 2/1989 | Gross et al. | |
| 4,817,242 | A * | 4/1989 | Rapp | 16/300 |
| 5,183,053 | A | 2/1993 | Yeh et al. | |
| 5,403,338 | A * | 4/1995 | Milo | 606/184 |
| 5,461,997 | A * | 10/1995 | Landen | 112/237 |
| 5,693,064 | A * | 12/1997 | Arnold | 606/184 |
| 5,782,851 | A * | 7/1998 | Rassman | 606/167 |
| 5,782,853 | A * | 7/1998 | Zeevi et al. | 606/187 |
| 5,792,163 | A | 8/1998 | Hitzig | |
| 5,794,344 | A * | 8/1998 | Poulos et al. | 30/113.1 |
| 5,827,316 | A * | 10/1998 | Young et al. | 606/185 |
| 5,951,572 | A | 9/1999 | Markman | |
| 6,027,512 | A | 2/2000 | Bridges | |

(Continued)

OTHER PUBLICATIONS

Micro-Mark "Micro Hand Drill" Product Description Sheet from www.micromark.com.

(Continued)

*Primary Examiner*—Gary Jackson
*Assistant Examiner*—Julie A Szpira
(74) *Attorney, Agent, or Firm*—Gordon & Jacobson, PC

(57) ABSTRACT

An improved tool for coring a portion of one or more hair follicles incorporates a mechanism that translates distal pushing forces that are applied to its handle to concomitant rotational movement of a hollow coring needle. Preferably, the force translation mechanism is realized by a helical threaded interface or a helical square rod interface between a handle and a rotating member that supports the needle. In another aspect, the tool includes a member that supports the hollow coring needle, the member having a cut-out that provides user access to the open proximal end of the needle. The tool can be made disposable by the use of injection molded plastic materials. The hollow coring needle is preferably realized from stainless steel and an anti-wear coating (such as a titanium nitride coating, a zirconium coating, or a diamond coating). In disposable applications, the tool is packaged in a sterilized manner, which avoids the need for the practitioner to sterilize the tool before use.

24 Claims, 3 Drawing Sheets

U.S. PATENT DOCUMENTS

| | | | |
|---|---|---|---|
| 6,059,807 A * | 5/2000 | Boudjema | 606/187 |
| 6,080,176 A | 6/2000 | Young | |
| 6,110,189 A | 8/2000 | Markman | |
| 6,572,625 B1 | 6/2003 | Rassman | |
| 2004/0092924 A1 * | 5/2004 | Vasa | 606/32 |
| 2004/0116942 A1 | 6/2004 | Feller | |
| 2005/0038465 A1 * | 2/2005 | Shraga | 606/182 |
| 2006/0041266 A1 * | 2/2006 | Sullivan et al. | 606/167 |
| 2006/0178678 A1 * | 8/2006 | Cole | 606/133 |

OTHER PUBLICATIONS

"Folicular Isolation Technique(Fit)" available at www.forhair.com/fit.htm.

* cited by examiner

TOOL FOR CORING PORTIONS OF ONE OR MORE HAIR FOLLICLES

BACKGROUND OF THE INVENTION

1. Field of the Invention

This invention relates methods and apparatus for coring hair follicle portions for the purpose of transplantation into areas where improved hair growth is desired.

2. State of the Art

A hair follicle is a tiny tubular structure in the skin, contiguous with the top skin layer, or epidermis, that includes a tubular canal, a bulb (or vestibule) within the dermis skin layer, one or more hair shafts, a sheath that surrounds the lower part (root) of the hair shaft(s), the sebaceous (oil) gland, and the muscle anchored to the follicle's side wall. Autologous hair transplants remove the patient's own hair follicles (or portions thereof) from one or more donor area(s) where there is relatively thick hair growth. The removed hair follicles (or portions thereof) are then implanted to one or more area(s) where improved hair growth is desired.

The traditional method for removing hair follicles in autologous hair transplants removes a patch of skin from the donor area, which is typically located in the back of the patient's head. The patch is selected so as to contain a plurality of hair follicles where each hair follicle consists, in the majority of cases, of a root plus one to three hairs. The patch is placed on ice to maintain it cool and hydrated in saline so as to not kill tissue. The patch is subsequently placed under a microscope where a technician slices and dissects individual hair follicles from the patch. Each discrete hair follicle is then implanted in an area of the head where hair growth is desired. The problems with this technique include scaring (i.e., the skin area where the patch is removed scars), and pain (i.e., removal of the patch is painful). Moreover, the area where the patch of skin was removed is devoid of hair and thus is cosmetically unappealing.

A new technique cores out hair follicle units directly from the donor area. This technique is advantageous because it is less painful than the patch removal technique and the scar that may form is very small and difficult to see. The hair follicle unit consists of the hair shaft, sheath, and bulb of an individual hair follicle structure. A coring device is placed around groups of one to four hairs removing an average of 50 percent of the intact hair follicular units of the group. Therefore, an average of 50 percent of the hair follicular units of the group is left behind to grow. Additionally, only 50-60 percent of the hair follicle units in the donor area are selected for coring, with the remaining percentage of hair follicle units left alone with no intervention. In this manner, any decrease in the visible density of hair in the donor area is virtually undetectable to the naked eye, which makes this new technique more cosmetically appealing than the patch removal technique. The problem with this technique is that it is very time consuming as well as very demanding on the physician. The tool normally used to core out the groups of hair follicle units is a hollow coring needle, typically between 0.5 and 2.0 mm in diameter, held by a pin vice handle. The physician first cuts the patient's hair in the donor area to the point where the hair is less than 2 mm long, and then the hollow coring needle is placed over a group of hair follicle units and manually rotated by finger movements while pressing gently downward. The manual rotation is performed in a repeating clockwise and counterclockwise manner until the group of hair follicle units is separated from the surrounding skin. This coring process is repeated for a multitude of hair follicle unit groups. Periodically, the cored-out hair follicle unit groups are removed from the head with forceps and placed in a saline solution on ice. The hair follicle unit groups are then transplanted in the usual manner. It is not unusual for the patient to require transplantation of 1,200 or more hair follicle units over a prolonged period of time, which may be six hours or more. Practitioners of this technique complain that the coring process is difficult on the fingers over this prolonged period of time and can lead to discomfort, fatigue stress and injury, including carpel tunnel syndrome and the like. Furthermore, the coring needles usually last for the coring of only 500 to 700 individual hair follicles before becoming dull. Lastly, the coring needles as well as the pin vice handle are required to be sterilized for each use.

SUMMARY OF THE INVENTION

It is therefore an object of the invention to provide a tool for coring a group of hair follicle units that reduces hand fatigue and stress experienced by the user.

It is another object of the invention to provide such a tool that employs a coring needle that remains sharp for the coring of a large number of individual hair follicle unit groups.

It is a further object of the invention to provide such a tool that is realized with a pre-sterilized and disposable handle and coring needles, thereby avoiding the need for the user to sterilize these components before use.

In accord with these objects, which will be discussed in detail below, an improved tool is provided that translates distal pushing forces that are applied to its handle to concomitant rotational movement of a hollow coring needle.

It will be appreciated that with such translation, the physician needs not perform rotation of the tool manually and thus avoids hand fatigue associated therewith. As a consequence, the tool enables more individual hair follicles to be harvested in a given amount of time while avoiding hand fatigue and stress commonly experienced with the use of the prior art tools.

According to a preferred embodiment of the invention, the rotation of the hollow coring needle is realized by a helical threaded interface or a helical square rod interface between a handle and a rotating member that supports the needle.

In another aspect of the present invention, the tool includes a member that supports the hollow coring needle, the member having a cut-out that provides user access to the open proximal end of the needle.

The tool can be made disposable by the use of injection molded plastic materials, such as polycarbonate, nylon, rigid polyurethane, Plexiglas, polyacetal, acrylonitrile butadiene styrene (ABS), and the like. The hollow coring needle is preferably realized from stainless steel, titanium nitride, zirconium, diamond tipped stainless steel, or any other material commonly used for needles, knives, drills and other tooling that is required to be sharp for prolonged periods of use. In disposable applications, the tool (including the handle, rotating member and one or more needles) is packaged in a sterilized manner, which avoids the need for the practitioner to sterilize the tool before use.

Additional objects and advantages of the invention will become apparent to those skilled in the art upon reference to the detailed description taken in conjunction with the provided figures.

DETAILED DESCRIPTION

As used herein, the term "distal" is generally defined as in the direction of the patient, or away from a user of the device. Conversely, "proximal" generally means in the direction away from the patient, or toward the user of the device.

Figure 1:
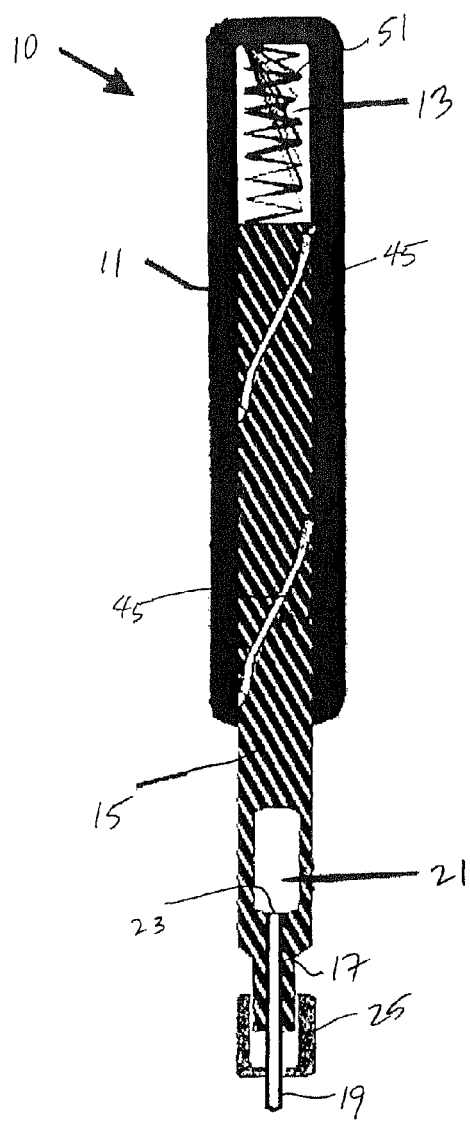
FIG. 1 is a schematic cross-sectional diagram of a hand tool for coring a group of hair follicle units from a patient's scalp in accordance with the present invention.

Turning now to FIG. 1, there is shown a tool 10 that cores a group of hair follicle units from a donor area of the patient's scalp for transplantation to an area where improved hair growth is desired. The tool 10 includes a handle 11 with an interior cavity 13. The proximal end of a rotating member 15 fits within the interior cavity 13. The distal end of the rotating member 15 includes a nose 17 that supports a hollow coring needle 19. The nose 17 can include a throughbore 18 designed to support a coring needle 19 of a specific outside diameter as shown. Alternatively, the nose 17 can be realized by an adjustable collet, chuck or other fastening means that can be adjusted to support a variety of hollow coring needles of different outside diameters. In the preferred embodiment, the coring needle 19 has an inside diameter in the range between 0.3 mm and 0.9 mm (most preferably on the order of 0.75 mm) and an outside diameter in the range between 0.5 mm and 1.5 mm (most preferably on the order of 1.0 mm). Such diameters enable the physician to core a group of one to four hair follicle units. Other diameters can be used.

A cut-out 21 in the rotating member 15, which is proximally disposed relative to the open proximal end 23 of the hollow coring needle 19, provides the user with the ability to clean out hair follicle units that may work their way up the coring needle 19 during use.

Figure 2:
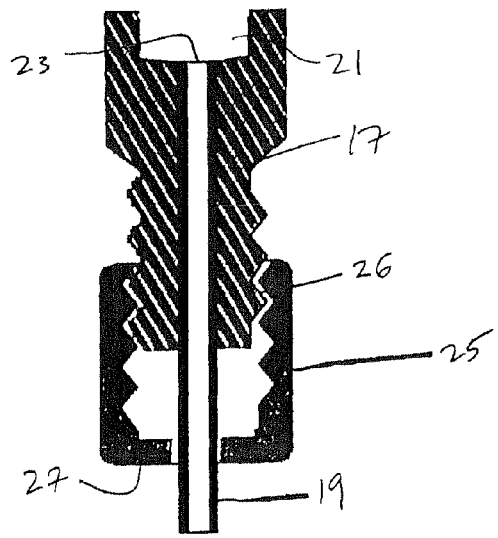
FIG. 2 is a schematic cross-section diagram of the nose portion of the hand tool of FIG. 1.
Figure 3:
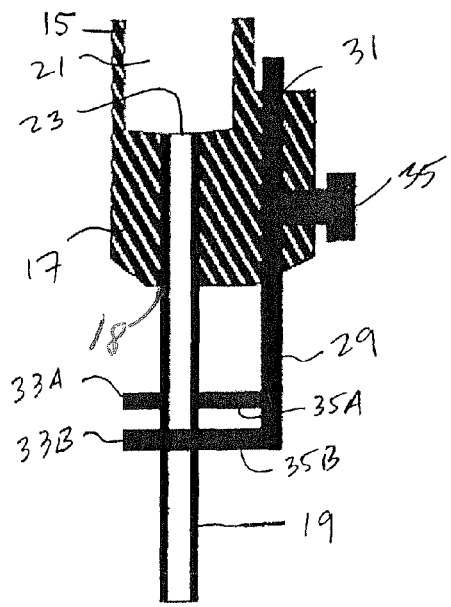
FIG. 3 is a schematic cross-sectional diagram of an alternate embodiment of the nose portion of hand tool of FIG. 1.

Preferably, an adjustable mechanism is mated to the nose 17 that defines the maximum depth that the coring needle 19 can penetrate into the scalp during use. In one embodiment as shown in FIGS. 1 and 2, the adjustable mechanism is realized by a collar 25 whose position along the longitudinal axis of the rotating member 15 is controlled by a threaded interface 26 between the collar 25 and nose 17 as shown in FIG. 2. In this configuration, manual rotation of the collar 25 adjusts the axial position of the collar 25 relative to the distal end of the nose 17. The distance between the distal "stop" surface 27 of the collar 25 and the distal tip of the coring needle 19 defines the maximum depth that the coring needle 19 can penetrate into the scalp during use. In another embodiment shown in FIG. 3, the adjustable mechanism is realized by a fork-like member 29 that has an elongate part 31 that extends distally from the nose 17 to bifurcations 33A, 33B that extend in a transverse direction relative to the longitudinal axis of the rotating member 15. The coring needle 19 passes through the space between the bifurcations 33A, 33B. The positions of the bifurcations 33A, 33B along the longitudinal axis of the rotating member 15 are adjustable and fixed by user manipulation of a set screw 35 that passes through a slot (not shown) in the elongate part 31 and into the nose 17. Contrary to the schematic view that is shown for simplicity of description, the distal surfaces 35A, 35B of the bifurcations 33A, 33B, respectively, are preferably positioned in a plane that lies orthogonal to the longitudinal axis of the rotating member 15.

In this configuration, the distal surfaces 35A, 35B act as stop surfaces that contact the scalp in use. The distance between these stop surfaces and the distal tip of the coring needle 19 defines the maximum depth that the coring needle 19 can penetrate into the scalp during use.

Figure 4:
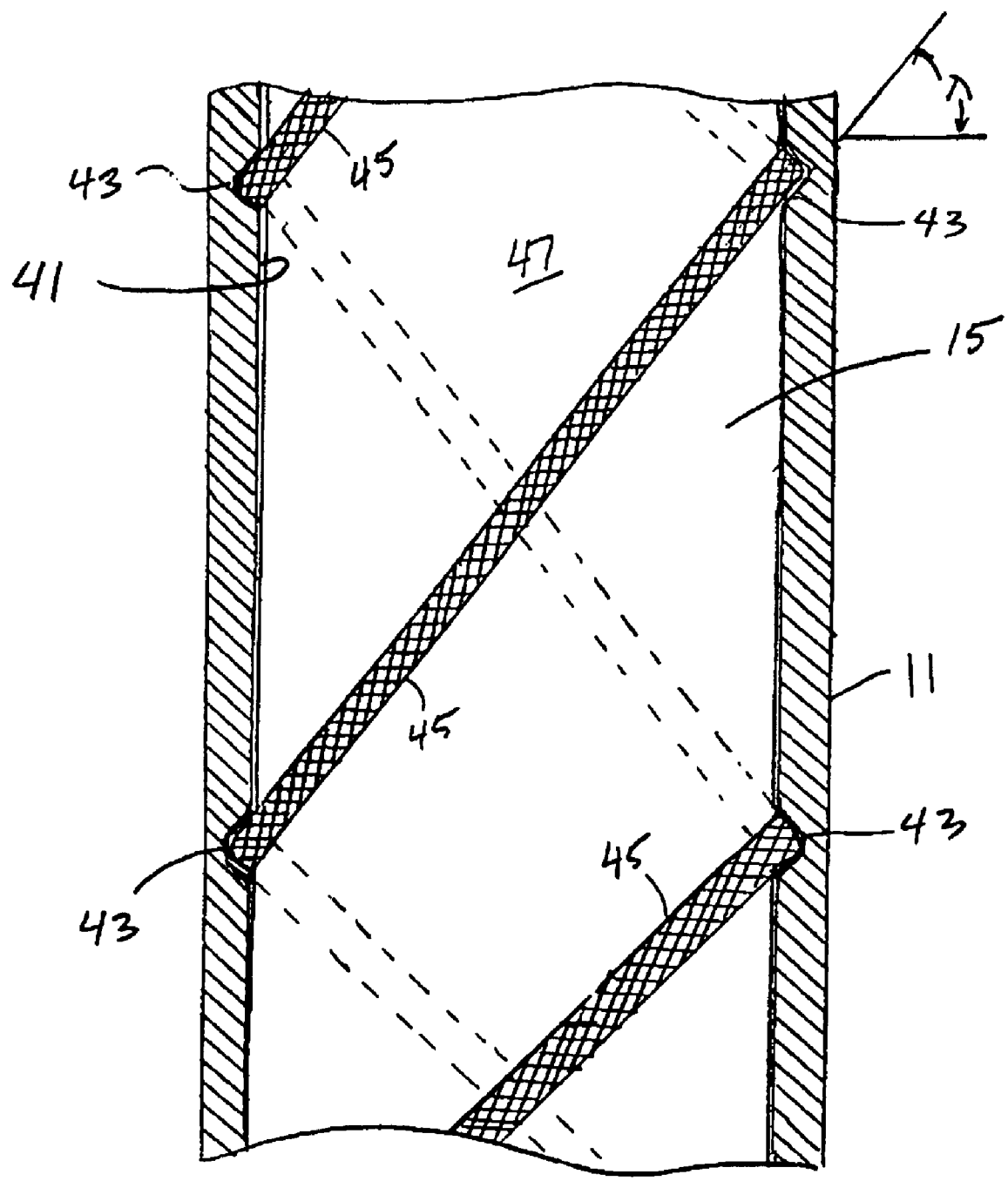
FIG. 4 is a schematic cross-sectional diagram of a helical threaded interface utilized by the hand tool of FIG. 1.

As best shown in FIG. 4, a portion of the inner circumferential surface 41 of the handle 11 includes at least one helical groove 43 (or thread), which is collectively referred to as a dog. The helical groove 43 (or thread) mates to a corresponding helical thread 45 (or groove) in a portion of the outer circumferential surface 47 of the rotating member 15, which is referred to collectively as a spline. Referring to FIG. 1, a spring 51 is provided within the interior cavity 13 preferably between the rotation member 15 and the proximal end of the handle 11.

During use, the distal open end 23 of the hollow coring needle 19 is placed over a group of hair follicle units (e.g., a group of one to four hair follicle units) and the user applies an axial force to the handle 11 that pushes it distally toward the scalp. The helical groove(s) and thread(s) of the dog and spline cooperate to rotate the rotating member 15 relative to the handle 11 when the user applies this axial pushing force. The rotation of the rotating member 15 is transferred to the hollow coring needle 19 supported by the nose 17 of the rotating member 15. The axial pushing force applied to the handle 11 is transferred to the hollow coring needle 11, thereby pushing the hollow coring needle 15 distally toward the scalp. The combination of the rotation and axial pushing force applied to the hollow coring 15 needle aids in coring out the group of hair follicle units with the hollow coring needle 19.

Figure 5:
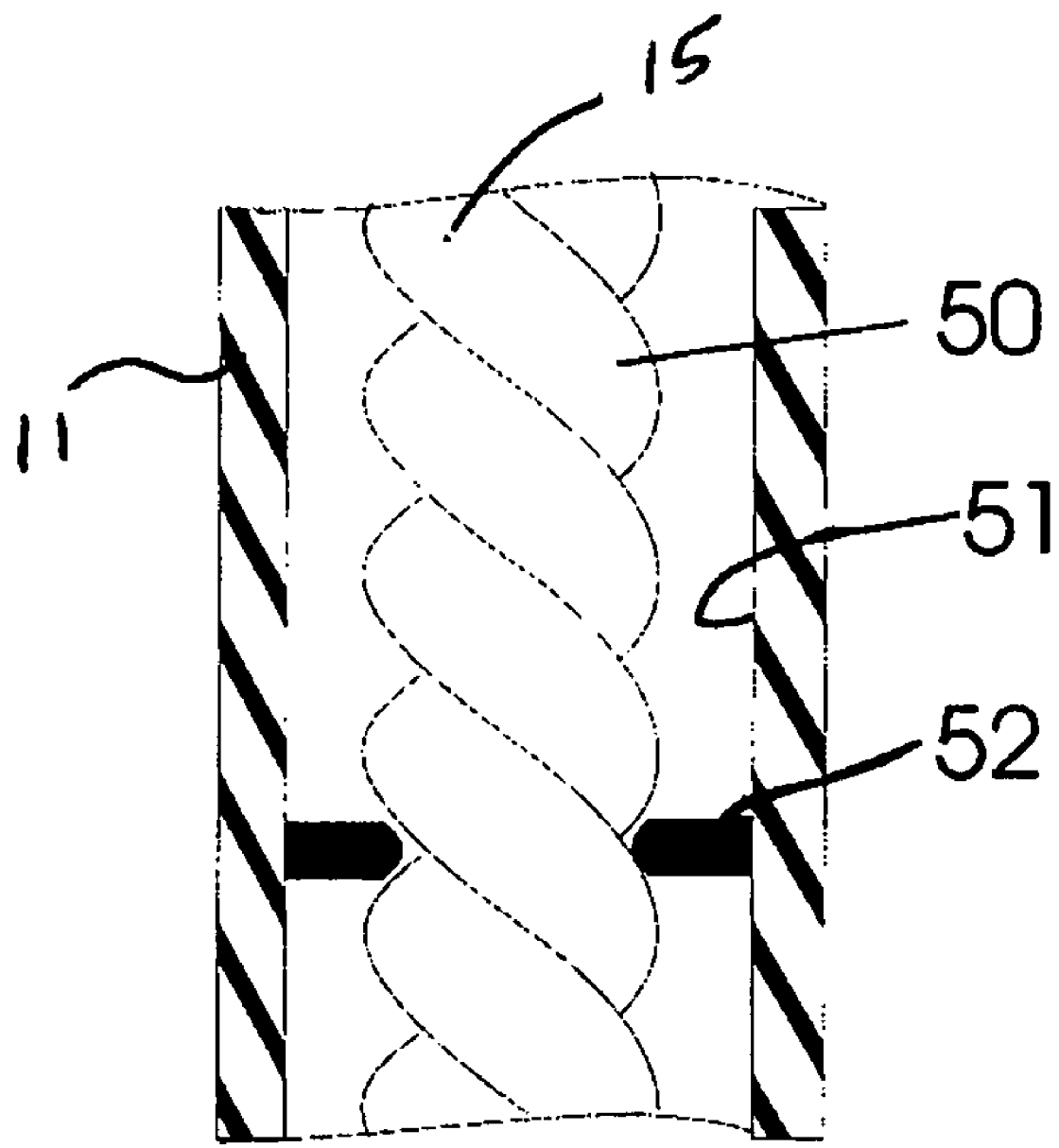
FIG. 5 is a schematic cross-sectional diagram of a helical square rod interface that can be utilized by the hand tool of FIG. 1.

Alternatively, the helical thread and groove interface can be substituted with a helical square rod interface as shown in FIG. 5. In this configuration, the rotating member 15 includes a spline 50 that is axially located within the interior cavity 13 of the handle 11. The spline 50 is constructed of helical square rod (i.e., a square bar stock that is twisted into a helix). One or more dogs 52 (one shown) are rigidly attached to the interior wall of the handle 11. The dog 52 consists of a relatively thin plate with a square hole in the center. The spline 50 is threaded through the square hole of the dog 52. Similar to the operation of the helical thread and groove interface of FIG. 4, the spline 50 is rotated when the handle 11 is axially pushed in the distal direction, thereby causing rotation of the rotating member 15 and the coring needle 19 supported thereby.

During its rotation, the rotating member 15 is translated proximally relative to the handle 11 along the longitudinal axis. The spring 51 counteracts this translation and operates to return the rotating member 15 to its initial position along the longitudinal axis when the user ceases to apply the axial pushing force to the handle 11.

The coring process is repeated to core out a number of hair follicle unit groups. Periodically, the cored-out hair follicle units are removed from the scalp with forceps and placed in a saline solution on ice. The hair follicle units are then transplanted in the usual manner to provide the desired hair growth.

It can be appreciated by those skill in the art that the lead angle $\lambda$ of the dog and spline, where the angle $\lambda$ is the angle made by the helix of the thread (or groove) with respect to a plane perpendicular to the longitudinal axis of the dog and spline (FIG. 4), governs the amount of axial force and rotational force translated to the rotating member 15 in response to the axial push force applied to the handle 11. Other parameters, such as the force-deflection characteristics of the spring 51, also control the amount of axial force and rotational force translated to the rotating member 15 in response to the axial push force applied to the handle 11.

It can also be appreciated by those skilled in the art that the force-deflection characteristics of the spring 51 can be made user-adjustable by manipulation of a screw (not shown) that extends into the cavity and butts up against the proximal end of the spring 51. In this configuration, user manipulation of the screw translates the proximal end of the spring 51 along the longitudinal axis of the spring 51 and rotating member 15, thereby adjusting the force-deflection characteristics of the spring 51. When the proximal end of the spring 51 is translated distally, the spring force increases and the maximal deflection decreases. The increase of the spring force increases the amount of axial force translated to the rotating member 15 in response to the axial push force applied to the handle 11. The decrease of the maximal deflection of the spring decreases the travel of the rotating member 15 along its longitudinal axis. When the proximal end of the spring 51 is translated proximally, the spring force decreases and the maximal deflection increases. The decrease of the spring force decreases the amount of axial force translated to the rotating member 15 in response to the axial push force applied to the handle 11. The increase of the maximal deflection of the spring increases the travel of the rotating member 15 along its longitudinal axis.

Moreover, it can be appreciated by those skilled in the art that the dog and spline can readily be adapted such that the rotating member 15 rotates first in one direction and subsequently in the other direction. Moreover, the dog and spline can readily be adapted such that the rotating member 15 rotates at different rates along its axial path of travel, for example rotating at a higher rotational rate near its initial position and rotating at a lower rotational rate when disposed far from its initial position, or vice versa. Moreover, the handle 11 and rotating member 15 can readily be adapted to incorporate alternative translation-to-rotation mechanisms, such as a ball-bearing spline or other suitable mechanism.

It is also contemplated that the open proximal end of hollow coring needle 19 can extend proximally into the cut-out 21 to allow a user to attach a suction line thereto to aid in removing hair follicle units from the coring needle 19.

The materials of choice for the hair follicle unit coring tool of the present invention include metals such as stainless steel, titanium, etc. In the event that the tool is to be made disposable, injection molded plastic materials are preferred. Such plastic materials include polycarbonate, nylon, rigid polyurethane, Plexiglas, polyacetal, acrylonitrile butadiene styrene (ABS), and the like. The hollow coring needle is preferably realized from stainless steel and an anti-wear coating (such as a titanium nitride coating, a zirconium coating, or a diamond coating). Alternatively, the hollow coring needing can be realized from any other material commonly used for needles, knives, drills and other tooling that is required to be sharp for prolonged periods of use. In disposable applications, the tool (including the handle, rotating member and one or more needles) are packaged in a sterilized manner, which avoids the need for the practitioner to sterilize the tool before use.

Advantageously, the tool translates axial forces that are applied to the handle to concomitant rotational movement of the hollow coring needle. With such translation, the physician need not perform such rotation manually and thus avoid hand fatigue associated therewith. As a consequence, the tool enables the physician to harvest more hair follicle unit groups in a given amount of time while avoiding finger fatigue and stress commonly experienced with the use of the prior art tools.

There have been described and illustrated herein several embodiments of a tool for coring a portion of one or more hair follicles and a method of operating such tool for autologous hair transplantation. While particular embodiments of the invention have been described, it is not intended that the invention be limited thereto, as it is intended that the invention be as broad in scope as the art will allow and that the specification be read likewise. Thus, while particular dimensions and materials have been disclosed, it will be appreciated that other dimensions and materials can be used as well. In addition, while particular applications of the tool have been disclosed for autologous hair follicle unit harvesting of the scalp, it will be understood that the tool can readily be used for hair follicle unit harvesting in other areas of the body. Moreover, while particular mechanisms have been disclosed that are capable of manually adjusting the needle depth of the tool, it will be appreciated that other mechanisms could be used as well. It will therefore be appreciated by those skilled in the art that yet other modifications could be made to the provided invention without deviating from its spirit and scope as claimed.

What is claimed is:

1. A tool for coring out a portion of one or more hair follicles from a patient's body comprising:
    a hollow coring needle;
    a handle that defines an interior cavity, said handle having a proximal end and a distal end;
    a member having a proximal portion defining a proximal end and a distal portion defining a distal end, the distal portion of the member mechanically supporting the needle and defining a cut-out adjacent said proximal end of said needle, said cut-out extending through a sidewall of said member for allowing removal of the hair follicles, the proximal portion housed within said interior cavity of the handle and capable of translation and rotation relative to the handle therein, the handle and member having a helical interface therebetween capable of rotating and translating the handle and member relative to each other in response to a pushing force applied to the handle that pushes the handle distally toward the patient, whereby the handle translates as a unitary body relative to the member and rotation of the member rotates the needle supported by the member, said distal portion of said member having means for fixing said needle to said distal portion of said member, said means for fixing operably disposed distal of said distal end of said handle and including a throughbore defined by said distal portion of said member, said throughbore having a proximal end in open communication with said cut-out;
    a spring disposed within the interior cavity of the handle and proximally extending from the proximal end of the member, the spring counteracting proximal translation of the member relative to the handle; and
    means for manually adjusting maximum penetration depth of the needle, said means for manually adjusting operably disposed at or adjacent the distal end of said member.

2. A tool according to claim 1, wherein:
    the handle and member are elongate structures that share a common longitudinal axis, and the pushing force is applied along the common longitudinal axis.

3. A tool according to claim 1, wherein:
    the helical interface comprises one of a helical threaded interface and a helical square rod interface.

4. A tool according to claim 3, wherein:
    the helical threaded interface or the helical square rod interface is disposed on an outside circumferential surface of the proximal portion of the member and on an inside circumferential surface of the handle.

5. A tool according to claim 2, wherein:
    the member translates proximally relative to the handle in response to the pushing force applied along the common longitudinal axis of the handle and member.

6. A tool according to claim 5, further comprising:
means for manipulating the force-deflection characteristics of the spring.

7. A tool according to claim 1, wherein:
the member has a distal nose portion; and
the means for manually adjusting maximum penetration depth of the needle comprises a collar having a threaded interface with the distal nose portion, wherein position of the collar relative to the distal nose portion is adjusted by manual manipulation of the threaded interface therebetween.

8. A tool according to claim 1, wherein:
the member has a distal nose portion; and
the means for manually adjusting maximum penetration depth of the needle comprises an element having an elongate first portion that extends distally from the distal nose portion and bifurcations that extend in a transverse direction relative to the elongate first portion such that the needle passes between the bifurcations, the first portion having an interface with the distal nose portion, wherein position of the bifurcations relative to the distal nose portion is adjusted by manual manipulation of the interface between the first portion and the distal nose portion.

9. A tool according to claim 1, wherein:
the hollow coring needle has an outer diameter in the range between 0.5 mm and 1.5 mm and has an inside diameter in the range between 0.3 mm and 0.9 mm.

10. A tool according to claim 1, wherein:
at least a portion of the tool is realized from a metal.

11. A tool according to claim 10, wherein:
the metal is selected from the group including stainless steel and titanium.

12. A tool according to claim 1, wherein:
at least a portion of the tool is realized from an injection molded plastic material.

13. A tool according to claim 12, wherein:
the injected molded plastic material is selected from the group including: polycarbonate, nylon, rigid polyurethane, Plexiglas, polyacetal, acrylonitrile butadiene styrene (ABS).

14. A tool according to claim 1, wherein:
the needle is realized from a material selected from the group including: stainless steel, a titanium nitride coating, a, zirconium coating, and a diamond coating.

15. A tool according to claim 1, wherein:
the open proximal end of the needle extends proximally into the cut-out.

16. A tool according to claim 1, wherein:
the hollow coring needle has an outer diameter in the range between 0.5 mm and 1.5 mm and has an inside diameter in the range between 0.3 mm and 0.9 mm.

17. A tool according to claim 1, wherein:
at least a portion of the tool is realized from a metal.

18. A tool according to claim 17, wherein:
the metal is selected from the group including stainless steel and titanium.

19. A tool according to claim 1, wherein:
at least a portion of the tool is realized from an injection molded plastic material.

20. A tool according to claim 19, wherein:
the injected molded plastic material is selected from the group including: polycarbonate, nylon, rigid polyurethane, Plexiglas, polyacetal, and acrylonitrile butadiene styrene (ABS).

21. A tool according to claim 1, wherein:
the needle is realized from a material selected from the group including stainless steel, a titanium nitride coating, a zirconium coating, and a diamond coating.

22. A tool according to claim 1, wherein:
the handle and member translate in opposite directions.

23. A method for coring out a portion of one or more hair follicles from a patient's body, the method comprising:
providing a tool according to claim 1, said tool having a longitudinal axis;
placing an end of said hollow coring needle of said tool over a hair follicle unit of the patient;
applying an axial force to said handle of said tool in the direction of the longitudinal axis of said handle,
wherein, in response to said axial force along the longitudinal axis, said member of said tool automatically rotates relative to said handle and translates along the longitudinal axis toward the patient, whereby rotation of said member rotates said coring needle for coring out the hair follicle unit of the patient.

24. A method according to claim 23, wherein:
after coring out a number of hair follicle units, a hair follicle unit is removed from said cut-out defined at said distal portion of said member.

* * * * *